(12) United States Patent
Turner

(10) Patent No.: US 10,286,195 B2
(45) Date of Patent: May 14, 2019

(54) SURGICAL DRAIN SUTURED-IN-PLACE PREVENTION DEVICE

(71) Applicants: University of Maryland, Baltimore, Baltimore, MD (US); THE UNITED STATES OF AMERICA AS REP. BY THE DEPT OF VETERANS AFFAIRS, Washington, DC (US)

(72) Inventor: Douglas Turner, Fulton, MD (US)

(73) Assignees: University of Maryland, Baltimore, Baltimore, MD (US); The United States of America as Represented by the Department of Veterans Affairs, Washington, DC (US)

( * ) Notice: Subject to any disclaimer, the term of this patent is extended or adjusted under 35 U.S.C. 154(b) by 197 days.

(21) Appl. No.: 15/127,082

(22) PCT Filed: Mar. 18, 2015

(86) PCT No.: PCT/US2015/021174
§ 371 (c)(1),
(2) Date: Sep. 19, 2016

(87) PCT Pub. No.: WO2015/142998
PCT Pub. Date: Sep. 24, 2015

(65) Prior Publication Data
US 2017/0173311 A1    Jun. 22, 2017

Related U.S. Application Data

(60) Provisional application No. 61/955,241, filed on Mar. 19, 2014.

(51) Int. Cl.
| | | |
|---|---|---|
| *A61M 27/00* | (2006.01) | |
| *A61M 25/02* | (2006.01) | |
| *A61M 25/06* | (2006.01) | |

(52) U.S. Cl.
CPC ......... *A61M 27/00* (2013.01); *A61M 25/0668* (2013.01); *A61M 2025/0286* (2013.01);
(Continued)

(58) Field of Classification Search
CPC .............. A61M 27/00; A61M 2205/04; A61M 2205/60; A61M 2025/0286; A61M 2025/0681; A61M 25/0668
(Continued)

(56) References Cited

U.S. PATENT DOCUMENTS

| | | |
|---|---|---|
| 3,430,631 A | 3/1969 | Abramson |
| 3,753,439 A | 8/1973 | Brugarolas et al. |

(Continued)

OTHER PUBLICATIONS

International Search Report issued in corresponding International Patent Application No. PCT/US2015/021174 dated Jun. 22, 2015.

*Primary Examiner* — Andrew J Mensh
(74) *Attorney, Agent, or Firm* — Whiteford, Taylor & Preston, LLP; Gregory M. Stone

(57) ABSTRACT

The present invention discloses systems and methods to alert a medical operator that a surgical drain has been sutured in place within a patient's body. A readily removable sheath is provided at a distal end of a surgical drain. The sheath is configured to be placed within a surgical wound along with the surgical drain, and after the surgical drain is placed, to be removed from the surgical drain and withdrawn from the patient's body, leaving the surgical drain in place. As the medical operator attempts to withdraw the sheath from the drain and the patient's body, in the event that a suture has inadvertently passed through the body of the surgical drain, such inadvertently placed suture will obstruct the removal of the sheath, in turn alerting the medical operator that the surgical drain has been inadvertently sutured and allowing them to correct the drain placement during the same surgical procedure.

15 Claims, 5 Drawing Sheets

(52) U.S. Cl.
CPC . *A61M 2025/0681* (2013.01); *A61M 2205/04* (2013.01); *A61M 2205/60* (2013.01)

(58) Field of Classification Search
USPC .......................................................... 604/541
See application file for complete search history.

(56) References Cited

U.S. PATENT DOCUMENTS

| | | | |
|---|---|---|---|
| 3,777,761 | A | 12/1973 | Sheridan |
| 3,957,054 | A * | 5/1976 | McFarlane ........ A61M 25/0023 604/541 |
| 4,508,533 | A | 4/1985 | Abramson |
| 5,370,610 | A | 12/1994 | Reynolds |
| 8,439,893 | B2 | 5/2013 | Wakabayashi |
| 8,540,687 | B2 | 9/2013 | Henley et al. |
| 2001/0005784 | A1 | 6/2001 | Righetti |
| 2005/0228471 | A1 * | 10/2005 | Williams ............... A61N 1/057 607/126 |
| 2007/0049907 | A1 * | 3/2007 | Fischer, Jr. ....... A61M 25/0017 604/544 |
| 2008/0058853 | A1 | 3/2008 | Kieturakis et al. |
| 2009/0287181 | A1 * | 11/2009 | Kagan .............. A61B 17/12022 604/506 |
| 2013/0218135 | A1 * | 8/2013 | Dein .................... A61M 27/00 604/541 |

* cited by examiner

SURGICAL DRAIN SUTURED-IN-PLACE PREVENTION DEVICE

CROSS-REFERENCE TO RELATED APPLICATIONS

This application is based upon and claims benefit of co-owned U.S. Provisional Patent Application Ser. No. 61/955,241 entitled "Surgical Drain Sutured-in-Place Prevention Device", filed with the U.S. Patent and Trademark Office on Mar. 19, 2014 by the inventor herein, the specification of which is incorporated herein by reference.

FIELD OF THE INVENTION

The present invention relates generally to surgical drains, and more particularly to devices and methods for avoiding inadvertent and/or unintended suturing of surgical drains within a patient's body.

BACKGROUND OF THE INVENTION

Many surgeries require postoperative drainage of excess blood and other fluids from the operative field. To account for this, a surgical drain such as a Jackson-Pratt or Penrose drain is typically placed deep within the operative field at the end of an operation. The wound is then sutured together in the vicinity of, but not including, the drain. Several layers of closing sutures may be present depending upon how deep the drain is placed. Drains are typically removed between one to five days following surgery.

Surgical drains are generally made from silicone or rubber, such that they are at risk of being punctured by a suture needle. Occasionally, the sutures used to close the wound inadvertently encircle or capture the drain. This sutures the drain in place within the patient's body, and there is no way for the surgical team to know this has occurred until drain removal is attempted several days later. When this does occur, it necessitates a second surgery and accompanying increases in morbidity, length of stay, and even mortality.

In light of the foregoing issues, there is a need in the art for a device and method that timely alerts the surgical team that a drain has been sutured in place within a patient's body, such as within a surgical wound. This will enable the surgeon to reopen the operative area and free the drain while the patient is still under anesthesia from the first surgery, thereby reducing the chances for a second surgery and associated complications.

SUMMARY OF THE INVENTION

The present invention discloses systems and methods to alert a medical operator that a surgical drain has been sutured in place within a patient's body, which thus prevents leaving an inadvertently and/or unintendedly sutured surgical drain within the patient's body. A readily removable sheath is provided at a distal end of a surgical drain. The sheath is configured to be placed within a surgical wound along with the surgical drain, and after the surgical drain is placed, to be removed from the surgical drain and withdrawn from the patient's body, leaving the surgical drain in place. As the medical operator attempts to withdraw the sheath from the drain and the patient's body, in the event that a suture has inadvertently passed through the body of the surgical drain, such inadvertently placed suture will obstruct the removal of the sheath, in turn alerting the medical operator that the surgical drain has been inadvertently sutured and allowing them to correct the drain placement during the same surgical procedure.

In accordance with certain aspects of an embodiment of the invention, a system to alert a medical operator that a surgical drain has been sutured in place within a patient's body is provided, such system comprising a surgical drain having a drain distal end and a drain proximal end, and a sheath removably attached to and surrounding at least a portion of the surgical drain and having a sheath distal end and a sheath proximal end, the sheath distal end being positioned adjacent the drain distal end, and the sheath being movable toward the drain proximal end.

In accordance with further aspects of an embodiment of the invention, a method to alert a medical operator that a surgical drain has been sutured in place within a patient's body is provided, comprising the steps of: providing a surgical drain having a drain distal end and a drain proximal end, and a sheath removably attached to and surrounding at least a portion of the surgical drain and having a sheath distal end and a sheath proximal end, the sheath distal end being positioned adjacent the drain distal end, and the sheath being movable toward the drain proximal end; inserting the surgical drain and sheath into an operative wound of a patient; closing the operative wound around the sheath and the surgical drain with one or more sutures; and attempting to remove the sheath from the surgical drain by pulling the sheath toward the proximal end of the drain; wherein resistance against removal of the sheath from the surgical drain is indicative of a suture having passed through the drain within the surgical wound.

BRIEF DESCRIPTION OF THE DRAWINGS

The numerous advantages of the present invention may be better understood by those skilled in the art by reference to the accompanying figures in which.

DETAILED DESCRIPTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

The present invention provides devices and methods to warn a surgeon that a surgical drain has been sutured in place and/or to prevent leaving an inadvertently and/or unintendedly sutured surgical drain within a patient's body by warning a surgeon that a surgical drain has been sutured in place.

Figure 1:
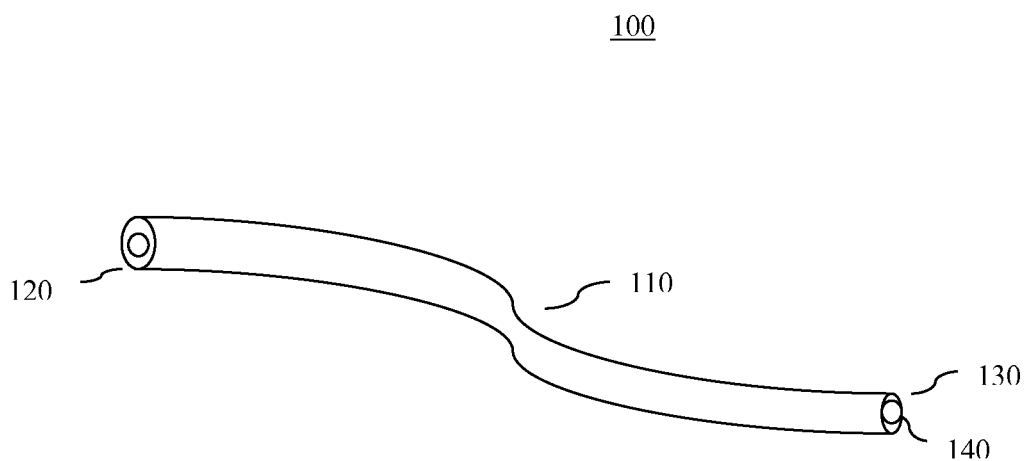
FIG. 1 is a perspective view of a prior art, standard surgical drain.

In accordance with certain aspects of an embodiment of the invention, a system to warn a surgeon that a surgical drain has been sutured in place and/or to prevent leaving an inadvertently and/or unintendedly sutured surgical drain within a patient's body includes a surgical drain and a surgical drain sleeve configured to be used with the surgical drain, and particularly for use with readily commercially available surgical drains of standard configurations known to those of ordinary skill in the art. FIG. 1 is a perspective view of an exemplary surgical drain 100, comprised of an elongated tube 110 having an inlet 120 at the distal end and an outlet 130 at the proximal end. Inlet 120 communicates with outlet 130 through one or more lumens 140, which one or more lumens 140 typically extend along the full length of the drain. As used herein, inlet 120 refers to the end of surgical drain 100 that is to be placed in the operative field, and outlet 130 refers to the end of surgical drain 100 that extends out of the patient's body for connection to a pump, a drainage reservoir, or other means for collecting fluid from the patient's body. Surgical drain 100 will typically have one or more round or generally rectangular lumens, and will typically be constructed of silicone, PVC, or rubber.

Figure 2:
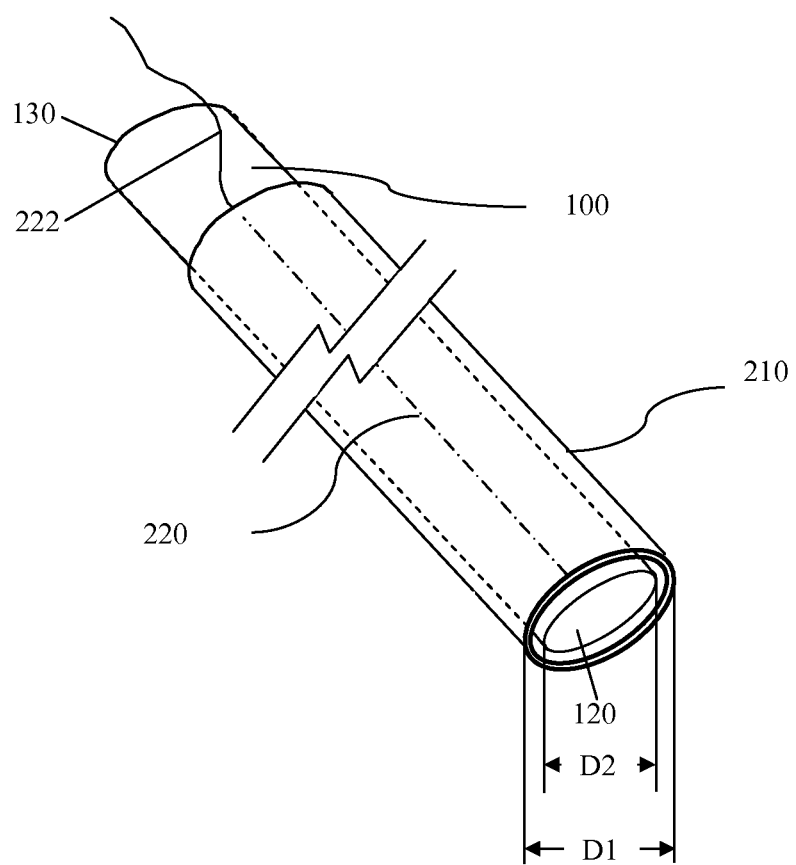
FIG. 2 is a perspective view of a system to warn a surgeon that a surgical drain has been sutured in place and/or to prevent leaving an inadvertently and/or unintendedly sutured surgical drain within a patient's body by warning a surgeon that a surgical drain has been sutured in place in accordance with certain aspects of an embodiment of the invention.
Figure 3:
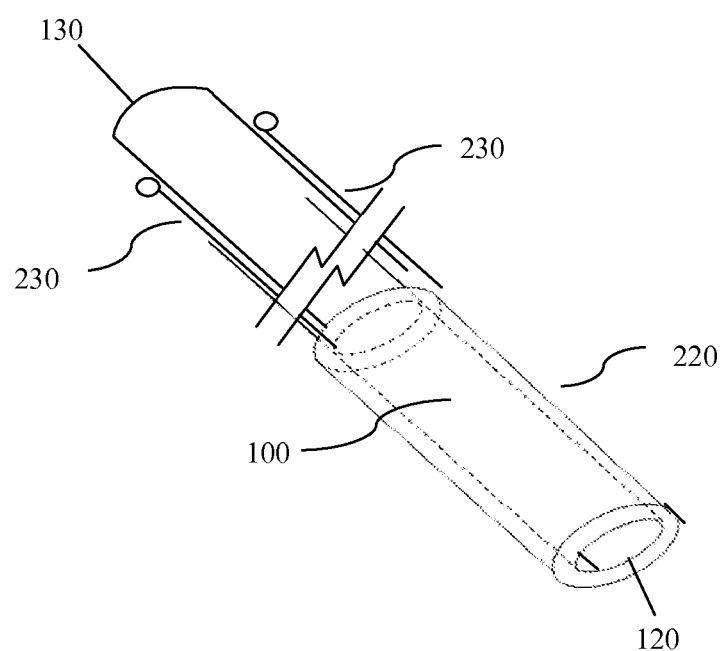
FIG. 3 is a perspective view of the system of FIG. 2 in accordance with further aspects of the invention.
Figure 4:
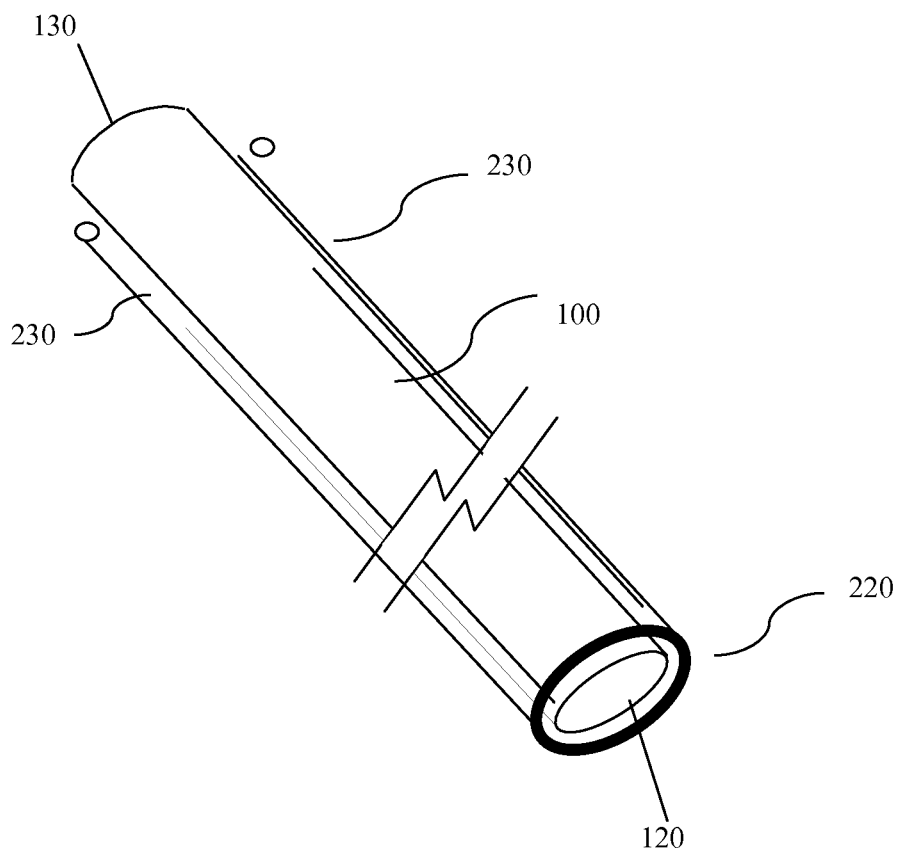
FIG. 4 is a perspective view of the system of FIGS. 2 and 3 in accordance with still further aspects of the invention.

FIGS. 2 through 4 show a system comprising a surgical drain 100 and sheath 210 in accordance with various aspects of the invention, wherein sheath 210 is readily removable from drain 100 after placement of the distal end of drain 100 having inlet 120 at the surgical site requiring drainage, so long as the sheath has not been sutured in place with the drain 100 or blocked from withdrawal along the drain 100 by a suture inadvertently placed through the drain 100 at a position proximal to sheath 210. As used herein, "readily removable" is intended to refer to a construction of sheath 210 that allows its temporary placement over at least a portion of a surgical drain, but extending around the entire outer circumference of the drain, and that may be and as configured to be removed from the drain after the drain is inserted into a patient's surgical wound by withdrawing the sheath in a direction generally parallel to the drain without disturbing the placement of the drain itself in the surgical wound. In such a readily removable condition, the inability of a surgeon or other medical personnel to fully remove the sheath after placement of the drain will indicate that the drain has been inadvertently affixed to the patient's body, such as from a suture inadvertently passing through the sheath and the drain, or through the drain at an axial position that is proximal to the sheath.

With particular reference to FIG. 2, a sheath 210 is provided having an inner diameter D1 that is slightly larger than the outer diameter D2 of the drain 100 to allow for minimal resistance when the sheath 210 is removed. In certain embodiments, a lubricant may be provided between the sheath 210 and drain 100 to further reduce friction to ease removal of sheath 210 from drain 100. As shown in FIG. 2, sheath 210 may comprise a solid cylindrical sheath that extends at least from the inlet of the drain to a location that is positioned outside of the patient's body. Sheath 210 is removable by sliding it over outlet 130. Sheath 210 may be configured to allow it to separate along the length of the cylinder. For example, a line of perforations 220 may be provided along the length of sheath 210. A pull string 222 may also be provided and affixed to sheath 210, such pull string 222 having a length sufficient to extend at least from a proximal end of the sheath to a location outside of the patient's body. Pull string 222 may optionally be embedded with the line of perforations 220 such that pulling on string 222 will also cause sheath 210 to split along perforation 220, with a portion of the pull string 222 remaining rigidly affixed to sheath 210 to allow it to be pulled from the patient's body. This eliminates the need to slide the sheath the entire length of the drain 100 and over the outlet 130.

As shown in FIG. 3, sheath 220 need not extend out of the patient's body, and instead may have a shorter length than that shown in FIG. 2. In this case, in order to provide for removal of sheath 220 from drain 100, one or more pull strings 230 may be joined to sheath 220. Pull strings 230 extend towards the proximal end of the drain 100, and have a length sufficient to extend outside of the patient. Pull strings 230 may thus be used by the surgical team to remove the sheath from within by pulling strings 230 toward the outlet 130 of drain 100.

In an exemplary embodiment, sheath 220 may have a length of approximately 0.25 inches to approximately six inches. Sheath 220 may be either longer or shorter than this range. For example, as shown in FIG. 4, sheath 220 may be in the form of a thin ring having a negligible length, with one or more pull strings 230 attached to the ring forming sheath 220.

In each of the foregoing configurations, sheath 220 is readily removable from drain 100 by pulling sheath 220 toward the proximal end of drain 100 at outlet 130, unless sheath 220 is obstructed from removal, such as by way of a suture that has either passed through the wall of the drain 100 at a location that is proximal to sheath 220, or that has passed through both sheath 220 and drain 100. If the surgeon or other medical personnel attempts to remove sheath 220 and encounters resistance, such resistance indicates to the operator that drain 100 has inadvertently been sutured to the patient's body, thus allowing the operator to immediately remedy the condition during the current surgical procedure.

The sheaths described above may further comprise additional features to ensure that a drain has not been sutured in place. For example, in certain embodiments the sheath 220 may include markings at the distal end for surgeon identification. Such markings allow the surgical team to identify the distal end of the sheath when it is removed, and thus confirm that the sheath 220 has been removed in its entirety. Markings may include, by way of non-limiting example, distinct colors or designs.

Another aspect of the invention provides for a surgical drain and sheath kit. The surgical drains provided in the kits may include specialized features to operate with a sheath. For example, if the sheath has pull strings, then they may be implanted or attached along the length of the drain wall.

Figure 5:
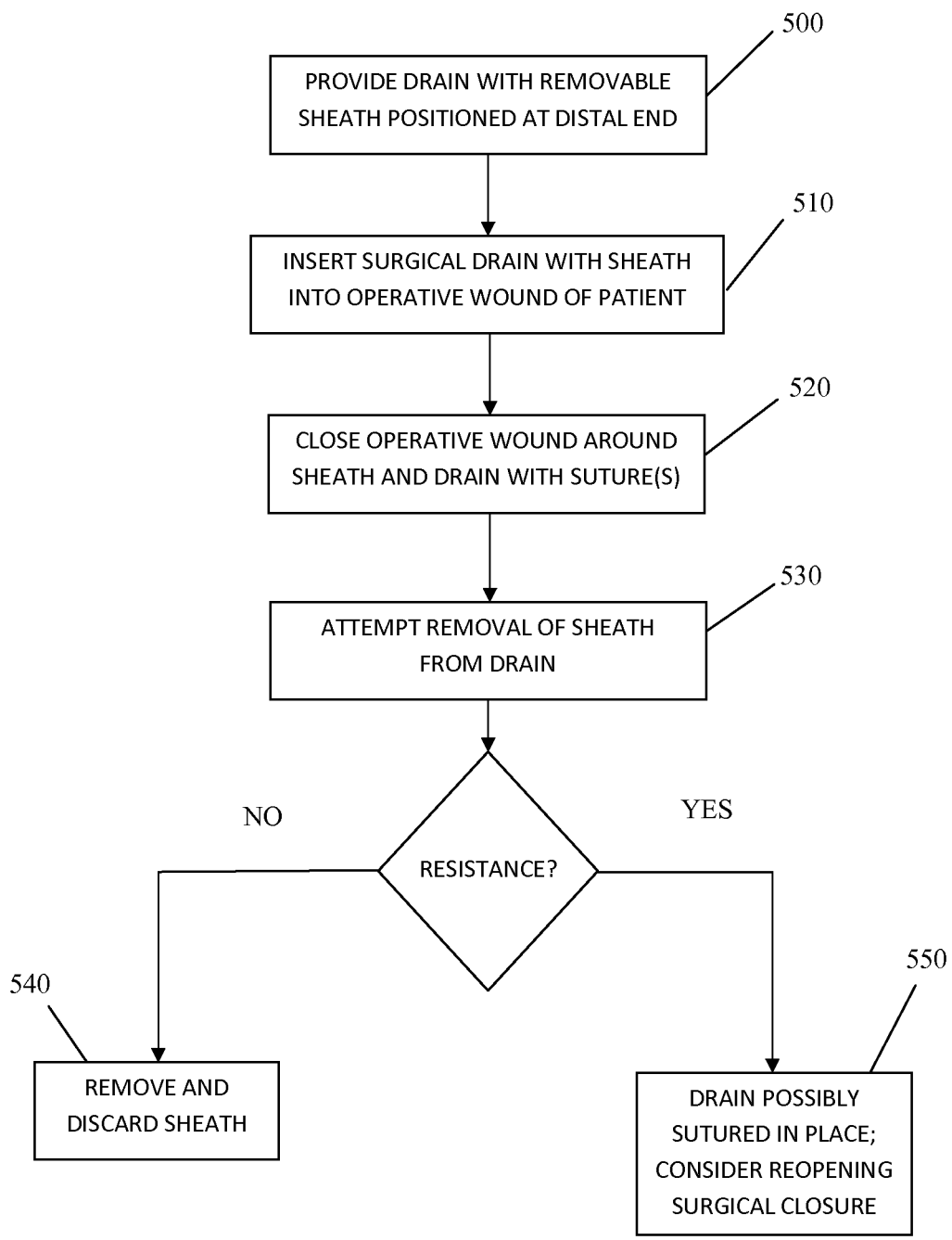
FIG. 5 is a schematic view of a method to prevent leaving an inadvertently and/or unintendedly sutured surgical drain within a patient's body by warning a surgeon that a surgical drain has been sutured in place in accordance with certain aspects of an embodiment of the invention.

In accordance with further aspects of the invention, a method for determining if a surgical drain has been sutured is provided and shown schematically in FIG. 5. At a first step 500, a surgical drain is provided with a readily removable sheath configured as detailed above and positioned at the distal end of the drain. Next, at step 510, the surgical drain is inserted with the readily removable outer sheath into an operative wound of a patient, and at step 520 the operative wound is closed around the sheath with one or more sutures. At step 530, the operator attempts to remove the outer sheath from the patient. If no resistance is encountered, then at step 540 the sheath is removed and discarded at step 540.

Likewise, if resistance is encountered, such resistance indicates that the surgical drain has been sutured in place, such that at step 550 the surgeon may remove the suture passing through the drain while the patient remains under anesthesia and as a part of the current operative procedure.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A system to alert a medical operator that a surgical drain has been sutured in place within a patient's body, comprising:
   a surgical drain having a drain distal end and a drain proximal end; and
   a sheath removably attached to and surrounding at least a portion of said surgical drain and having a sheath distal end and a sheath proximal end, said sheath distal end being positioned adjacent to said drain distal end, and said sheath being movable toward said drain proximal end.

2. The system of claim 1, said sheath having a line of perforation extending along at least a portion of said sheath.

3. The system of claim 2, wherein said line of perforation is configured to allow portions of said sheath to separate along a length of said sheath.

4. The system of claim 2, further comprising at least one pull string attached to said sheath.

5. The system of claim 4, wherein said pull string has a length dimension that is sufficient to allow said pull string to extend at least from the proximal end of said sheath to a position outside of a patient's body when said distal end of said drain is positioned at an intended drainage site within the patient's body.

6. The system of claim 1, further comprising at least one pull string attached to said sheath.

7. The system of claim 6, wherein said pull string has a length dimension that is sufficient to allow said pull string to extend at least from the proximal end of said sheath to a position outside of a patient's body when said distal end of said drain is positioned at an intended drainage site within the patient's body.

8. The system of claim 7, wherein said sheath is in the form of a circular ring.

9. The system of claim 1, wherein said sheath has a length dimension of between 0.25 inches and 6 inches.

10. The system of claim 1, further comprising a lubricant between an interior of said sheath and an exterior of said drain.

11. The system of claim 1, further comprising indicia on the distal end of said sheath.

12. The system of claim 1, wherein said sheath distal end is positioned in alignment with said drain distal end.

13. A method to alert a medical operator that a surgical drain has been sutured in place within a patient's body, comprising the steps of:
    providing a surgical drain having a drain distal end and a drain proximal end, and a sheath removably attached to and surrounding at least a portion of said surgical drain and having a sheath distal end and a sheath proximal end, said sheath distal end being positioned adjacent to said drain distal end, and said sheath being movable toward said drain proximal end;
    inserting the surgical drain and sheath into an operative wound of a patient;
    closing the operative wound around the sheath and the surgical drain with one or more sutures; and
    attempting to remove the sheath from the surgical drain by pulling the sheath toward the proximal end of the drain;
    wherein resistance against removal of the sheath from the surgical drain is indicative of one of the one or more sutures having passed through the drain within the surgical wound.

14. The method of claim 13, wherein said sheath distal end is positioned in alignment with said drain distal end.

15. The method of claim 14, wherein said steps of (i) inserting the surgical drain and sheath, and (ii) closing the operative wound are carried out while maintaining said sheath distal end in alignment with said drain distal end.

* * * * *